(12) United States Patent
Chaudhary et al.

(10) Patent No.: US 9,345,660 B2
(45) Date of Patent: May 24, 2016

(54) MICRO-EMULSIONS FOR THE TREATMENT OF RHEUMATIC DISORDERS

(75) Inventors: Manu Chaudhary, Panchkula (IN); Vijay Naithani, Panchkula (IN)

(73) Assignee: SUNEV PHARMA SOLUTION LIMITED, Panchkula (IN)

( * ) Notice: Subject to any disclaimer, the term of this patent is extended or adjusted under 35 U.S.C. 154(b) by 58 days.

(21) Appl. No.: 13/322,772

(22) PCT Filed: Jun. 4, 2010

(86) PCT No.: PCT/IN2010/000371
§ 371 (c)(1),
(2), (4) Date: Nov. 28, 2011

(87) PCT Pub. No.: WO2010/140170
PCT Pub. Date: Dec. 9, 2010

(65) Prior Publication Data
US 2012/0093888 A1    Apr. 19, 2012

(30) Foreign Application Priority Data

Jun. 5, 2009  (IN) .......................... 1153/DEL/2009

(51) Int. Cl.
| | |
|---|---|
| *A61K 9/00* | (2006.01) |
| *A61K 9/107* | (2006.01) |
| *A61K 36/00* | (2006.01) |
| *A61K 36/81* | (2006.01) |

(52) U.S. Cl.
CPC ............ *A61K 9/0014* (2013.01); *A61K 9/1075* (2013.01); *A61K 36/00* (2013.01); *A61K 36/81* (2013.01)

(58) Field of Classification Search
None
See application file for complete search history.

(56) References Cited

U.S. PATENT DOCUMENTS

| | | | | |
|---|---|---|---|---|
| 4,647,586 | A | 3/1987 | Mizushima et al. | 514/532 |
| 5,250,236 | A * | 10/1993 | Gasco | 264/4.4 |
| 5,494,668 | A | 2/1996 | Patwardhan | 424/195.1 |
| 5,683,698 | A | 11/1997 | Chavali et al. | 424/195.1 |
| 5,788,971 | A | 8/1998 | Togasaki | 424/195.1 |
| 5,854,291 | A | 12/1998 | Laughlin et al. | 514/626 |
| 5,888,514 | A | 3/1999 | Weisman | 424/195.1 |
| 5,908,628 | A | 6/1999 | Hou | 424/195.1 |
| 5,910,307 | A | 6/1999 | Kwak et al. | 424/195.1 |
| 5,916,565 | A | 6/1999 | Rose et al. | 424/195.1 |
| 6,638,522 | B1 | 10/2003 | Mulye | 424/439 |
| 6,638,537 | B2 | 10/2003 | Dennis et al. | 424/502 |
| 7,531,194 | B2 | 5/2009 | Wu et al. | 424/725 |
| 2003/0232095 | A1 | 12/2003 | Garti et al. | 424/725 |
| 2005/0208083 | A1 | 9/2005 | Annis | 424/400 |
| 2007/0036831 | A1 * | 2/2007 | Baker | 424/400 |

FOREIGN PATENT DOCUMENTS

| | | | | |
|---|---|---|---|---|
| EP | 0152945 | A2 | 8/1985 | ............ A61K 9/10 |
| KR | 20010086473 | A | 9/2001 | ............ A61K 31/05 |
| WO | WO 00/17294 | A1 | 3/2000 | ............ C11B 9/00 |
| WO | WO 02085394 | A1 * | 10/2002 | |
| WO | WO 2005027872 | A2 * | 3/2005 | |
| WO | WO 2007/060177 | A1 | 5/2007 | ............ A61K 9/113 |
| WO | WO 2009020280 | A1 * | 2/2009 | |
| WO | WO 2009/029046 | A1 | 3/2009 | ............ A61K 8/00 |

OTHER PUBLICATIONS

G. Singh, I. P. S. Kapoor, S. K. Pandey, U. K. Singh and R. K. Singh. Studies on Essential Oils: Part 10; Antibacterial Activity of Volatile Oils of Some Spices. Phytother. Res. 16, 680-682 (2002).*
Young-Joon Surh. Anti-tumor promoting potential of selected spice ingredients with antioxidative and anti-inflammatory activities: a short review. Food and Chemical Toxicology 40 (2002) 1091-1097.*
International Search Report mailed Oct. 19, 2010, in International Application No. PCT/IN2010/000371, pp. 1-4.
Long, L., et al., Herbal medicines for the treatment of osteoarthritis: a systematic review, dated 2001, pp. 779-793, vol. 40, British Society for Rheumatology, Rheumatology.
Soeken, K. L., et al., Herbal medicines for the treatment of rheumatoid arthritis: a systematic review, dated 2003, pp. 652-659, vol. 42, British Society for Rheumatology, Rheumatology.
Teekachunhatean, S., et al., Chinese herbal recipe versus diclofenac in symptomatic treatment of osteoarthritis of the knee: a randomized controlled trial, dated Dec. 13, 2004, pp. 1-8, vol. 4, BioMed Central, BMC Complementary and Alternative Medicine.

* cited by examiner

*Primary Examiner* — Frederick Krass
*Assistant Examiner* — Michael P Cohen
(74) *Attorney, Agent, or Firm* — Ladas & Parry LLP

(57) ABSTRACT

A formulation to treat rheumatic disorders and related infections is provided. The formulation is a micro-emulsion including at one or more of an active ingredients. The active ingredient includes one or more of an essential oil mixed with an aqueous phase along with one or more of a surfactant and one or more of a co-surfactant. The co-surfactant is medicated by an extract of one or more of an herb.

12 Claims, 5 Drawing Sheets

Table1

| Period (months) | Description | Odour | Solubility (Insoluble in water but freely soluble in ethanol | Specific gravity (Between 0.90 and 1.10) | pH (5.5-7.5) | Viscosity (at 100 rpm) (NMT 20) | Light Absorption (at 520 nm) (NMT 3.5) | Z-average size NMT 500 nm | PDI NMT 0.500 | Zeta potential Between -0.10 to -0.80 |
|---|---|---|---|---|---|---|---|---|---|---|
| Initial | Clear, transparent, pink to red viscous liquid | Strong aromatic | Complies | 0.99 | 6.79 | 11.1 | 2.8 | Complies | Complies | Complies |
| 3 | Clear, transparent, pink to red viscous liquid | Strong aromatic | Complies | 0.99 | 6.78 | 11.1 | 2.81 | Complies | Complies | Complies |
| 6 | Clear, transparent, pink to red viscous liquid | Strong aromatic | Complies | 1 | 6.77 | 11.2 | 2.807 | Complies | Complies | Complies |
| 9 | Clear, transparent, pink to red viscous liquid | Strong aromatic | Complies | 1 | 6.76 | 11.2 | 2.809 | Complies | Complies | Complies |
| 12 | Clear, transparent, pink to red viscous liquid | Strong aromatic | Complies | 1 | 6.76 | 11.2 | 2.811 | Complies | Complies | Complies |
| 18 | Clear, transparent, pink to red viscous liquid | Strong aromatic | Complies | 1.01 | 6.76 | 11.2 | 2.812 | Complies | Complies | Complies |
| 24 | Clear, transparent, pink to red viscous liquid | Strong aromatic | Complies | 1.01 | 6.75 | 11.3 | 2.814 | Complies | Complies | Complies |

Table 2

FIG. 2

| Sr. No | Name of Microorganism | Zone of Inhibition (In mm) | | |
|---|---|---|---|---|
| | | 30 µl | 60 µl | 100 µl |
| 1 | S. aureus (MTCC No:737) | 10.94 | 12.60 | 13.90 |
| 2 | E. coli (MTCC No: 1687) | 12.49 | 14.55 | 16.90 |

Table 3

| Sample Name | Code | Major Ingredients | NO (% Inhibition) | Superoxide anion radical (%Inhibition) | Metal chelating activity (%) | Free radical scavenging activity (%DPPH activity) | Hydroxyl radical scavenging assay (% Inhibition of DNA damage) |
|---|---|---|---|---|---|---|---|
| Formulation of Example 7 | Formulation of Example 7 | Wintergreen oil, Camphor oil, Eucalyptus oil, Menthol, Apium graveolens, Boswellia serrata & Vitex negundo | 64.84% | 71.92% | 48.59% | 61.54% | 75.66% |
| Brand 1 (Fast Relief) | A | Wintergreen oil, Mint, Camphor oil, Eucalyptus oil & Tarpeen oil | 52.28% | 59.29% | 45.77% | 60.12% | 64.81% |
| Brand 2 (Rumalya) | B | Wintergreen oil, Mentha arvensis, Pinus roxburghii & Cinnamomum zeylanicum | 54.34% | 72.74% | 49.19% | 53.49% | 47.62% |
| Brand 3 (Volini) | C | Methyl Salicylate, Menthol & Diclofenac | 49.77% | 69.95% | 32.86% | 55.28% | 36.84% |
| Brand 4 (Moov) | D | Wintergreen oil, Pudine ka phool, Tarpin oil & Nilgiri oil | 50.91% | 71.73% | 12.70% | 39.18% | 75.26% |
| Brand 5 (Arflur) | E | Methyl Salicylate, Menthol & Aceclofenac | 46.35% | 71.08% | 19.35% | 60.82% | 48.54% |
| Brand 6 (Diclowin Plus) | F | Methyl Salicylate, Menthol & Diclofenac | 45.21% | 67.37% | 33.87% | 56.35% | 44.31% |

Table 4

FIG. 6

MICRO-EMULSIONS FOR THE TREATMENT OF RHEUMATIC DISORDERS

BACKGROUND

1. Field of Invention

The embodiments herein generally relates to a topical formulation useful for the treatment of pain, inflammation and symptoms related to gout, rheumatic disorders, and, more particularly to a micro-emulsion based synergistic herbal formulation and a process of preparation of the same in pharmaceutical acceptable dosage forms. Further more specifically, the embodiments is concerned with the therapeutic properties of the formulation to be applied topically for the treatment of rheumatic disorders and related infections including arthritis, gout, fibromyalgia, ankylosing spondylitis, osteomyelitis, bone TB. Even more specifically, the present embodiment is concerned with the topical treatment using the said formulations having rapid and efficient penetration, increased rate of absorption, increased bioavailability, low irritation, better efficacy and synergistic bacteriostatic activity of therapeutic agents.

2. Description of the Related Art

Rheumatic disorders, including arthritis, gout, fibromyalgia, ankylosing spondylitis are characterized by inflammation and pain in bones, joints, muscles, and related connective tissues. Arthritis is a common progressive disease of various etiologies. Rheumatoid arthritis is a chronic syndrome characterized by non-specific usually symmetric inflammation of the peripheral joints, potentially resulting in progressive destruction of articular and per-articular structures leading to deformity. There is a wide spectrum of disease severity but many patients run a course of intermittent relapses and remissions with an overall pattern of slowly progressive joint destruction. Persistent inflammation produces symptoms and damages tissue causing loss of cartilage, erosion of bone matter and subluxation of joint. This results in a high degree of morbidity resulting in disturbed daily life of the patient. Bone and joint inflammation is a scourge of both animals and humans. Those who suffer from inflammation experience pain and discomfort and may, in advanced cases, lose the effective use of inflamed joints.

A bacterial injection of a joint can also cause a severe and potentially destructive form of arthritis, often referred to as septic arthritis. Bacterial joint infections can be caused by a number of different organisms and can occur in both natural and artificial joints (eg, after a knee replacement).

Natural ingredients, e.g., herbs, have been used to treat bone and joint inflammation, (Long et al; Rheumatology 2001; 40: 779-793, Teekachunhatean et al; BMC Complemetary and Alternative Medicine 2004; 4:19) especially in eastern countries; and, increasingly, in western countries. Some of the commonly used herbs are extracts of *Withania somnifera, Boswellia serrata, Zingiber officinale, Curcuma longa* in tablet form (Soeken et al; Rheumatology 2003; 42: 652-659). Compositions composed of natural ingredients used for the treatment of pain and inflammation are disclosed, in U.S. Pat. Nos. 5,494,668; 5,683,698; 5,916,565; 5,888,514; 5,854,291; 5,908,628; 5,788,971, 5,910,307, 7,531,194 and PCT/SG2007/000284. Prior arts disclose various formulations in oral/topical form using herbal ingredients but still fail to solve the problem of spreading this kind of diseases which are reported to be growing at rate of 13.67%. Arthritis limits the activity of over 7 million people in US alone, and is second only to heart disease as a cause of work disability. Recent estimates, place the direct medical cost of arthritis at $15.2 billion per year, with total costs of medical care and lost wages exceeding $64 billion.

This is because there was technical barrier to develop herbal formulations in new drug delivery system as disclosed in the current embodiment that can provide an additional benefits in terms of technological advancements.

Prevalent treatment of Rheumatoid diseases includes first line drugs for control of pain and inflammation classified as non-steroidal, anti-inflammatory drugs (NSAIDS). Secondary treatment include corticosteroids, slow acting anti-rheumatic drugs (SAARDS) or disease modifying (DM) drugs include penicillin amine like drugs such as cyclophosphamide, methotrexate, gold salts, azothioprine, levamisole. All these drugs have severe side effects and most of them are cytotoxic.

Some of the micro-emulsion based formulations have been disclosed in U.S. Pat. Nos. 6,638,537, 6,638,522, 4,647,586 using phenyl butazone, sulindac, penicillamine, salsalate, piroxicam, azathioprine, indomethacin, meclofenamate sodium, gold sodium thiomalate, ketoprofen, diclofenac, auranofin, aurothioglucose, tolmetin sodium, colchicine, allopurinol, cyclosporin and other NSAIDs. These formulations are for oral administration only and thus cause huge side effects, and have complications related to multi drug administration, thus fail to provide safe and effective therapy for better patient compliance. Frequently, anti-inflammatory medicaments cause abnormalities in the bowel tract e.g. bleeding.

The drugs used till date have limited advantages and their effects mainly of short term duration and there are many disadvantages in the use of these drugs over extended periods of time. Further the drugs used at present are costly and have low-benefit risk ratio. The ideal formulation to modify the progress of the disease have not been found heretofore.

SUMMARY OF THE INVENTION

In view of the forgoing, a formulation to treat rheumatic disorders and related infections is provided. The formulation is a micro-emulsion including at one or more of an active ingredients. The active ingredient includes one or more of an essential oil mixed with an aqueous phase along with one or more of a surfactant and one or more of a co-surfactant. The co-surfactant is medicated by an extract of one or more of a herb.

The micro-emulsion may include the essential oil as an oil phase and a water as the aqueous phase. The oil phase and the aqueous phase is in a ratio of 14 to 4:1; the surfactant and the co-surfactant in a ratio of 0.5:1 to 1:1.5; the surfactant and the co-surfactant in a ratio of 0.5:1 to 1:1.5; the surfactant is one or more of a non-ionic long chain polymer; a particle size of the formulation is 0.005 to 0.5 microns; a Poly Dispersity Index (PDI) of the formulation is 0.100 to 0.300; and a Zeta potential of the formulation is 0.100 to 0.500.

The essential oil may be selected from a group consisting of a wintergreen oil or a *gaultheria precumbens* oil, *cinnamomum camphora* oil, an *eucalyptus* oil, a camphor oil, a *cedrus* oil, a sesame oil, a terpentine oil, a dove oil, a garlic oil, a *cyperus* oil, a basil oil, a lavender oil, a rosemary oil, a mint oil, a Geranium oil. The essential oil is mixed with *Capsicum Anuum* or menthol and the aqueous phase; and the essential oil is systemically absorbed.

The co-surfactant may be an alcohol including the extract of one or more of the herb. The herb may be selected from a group consisting of *Apium graveolens, Withania somnifera, Allium sativum, Myristica fragrans, Piper nigrum, Zingiber*

*officinale, Piper longum, Cinnamomum zeylanicum, Cinnamomum tamala, Vitex negundo, Boswellia serrata, Cissus quadrangularis, Terminalia arjuna, Pluchea lanceolata, Commiphora mukul, Sida acuta, Cedrus deodara, Tinospora cordifolia, Cyperus rotundus, Trachyspermum ammi, Embelia ribes, Piper longum.*

The non-ionic long chain polymer surfactants may be one of a Tween 80 or a Tween 20. The weight ratio of the Tween 80:the Tween 20 is 90:20 to 20:90.

The water in oil microemulsion may include winter green oil in an amount 20±3% as volume/volume, a camphor oil in an amount 5±3% as volume/volume, in *eucalyptus* oil in an amount 6±3% as volume/volume along with weight/volume range of the Menthol in 5±3%. The menthol is dissolved in the essential oils as the oil phase; the water may be in range of 7±5% as aqueous phase; the long chain polymer surfactant includes the Tween 80 and the Tween 20 in volume/volume ratio of 90:20 to 20:90; the co-surfactant may be one or more of an alcohol including an extract which is medicated by one or more of *Vitex negundo, Boswellia serrata* and *Apium graveolens* in the ratio of 1:1:1; and the formulation may have a particle size in the range of ≤0.005 micron, a zeta potential is ≤5-0.268 and poly dispersity index is ≤0.136.

The formulation may be energy efficient and may be prepared as the water in oil micro-emulsion; the water may be the aqueous phase; ratio of the aqueous phase and the oil phase may be 1:4 to 4:1; the formulation may have a particle size≤0.5 micron, a zeta potential≤−0.350 and poly dispersity index is ≤0.150.

The water in oil micro-emulsion may includes a *Gaultheria precumbens* oil in an amount 13±3% as volume/volume, a *Cedrus deodara* oil in an amount 1±3% volume/volume, a *Cyperus rotundus* oil in an amount 1±3% volume/volume, a *Cinnamomum camphora* oil in an amount 4±3% volume/volume, an *eucalyptus* oil in an amount 7±3% volume/volume along with weight/volume range of *Capsicum Anuum* in 0.05±3% and menthol in 4±3% dissolved in the essential oils as oil phase; the water is in range of 7±5% as aqueous phase; the long chain polymer surfactant may include the Tween 80 and the Tween 20 in volume/volume ratio of 90:20 to 50:50; the co-surfactant may be one of an alcohol which is medicated and including an extract of *Apium graveolens* and a ratio of the surfactant to the co-surfactant is 0.56:1 with a HLB value of 16.7; and the formulation has a particle size in the range of ≤0.005 micron, a zeta potential is ≤−0.268 and poly dispersity index is ≤0.136.

The formulation may be used for the treatment of rheumatic disorders and related conditions may include Lupus, Sjögren's syndrome, scleroderma (systemic sclerosis), dermatomyositis, polychondritis, polymyositis, polymyalgia rheumatica, osteoarthritis, septic arthritis, The water in oil micro-emulsion may include winter green oil in an amount 20±3% as volume/volume, a camphor oil in an amount 5±3% as volume/volume, an *eucalyptus* oil in an amount 6±3% as volume/volume along with weight/volume range of the menthol in 5±3%. The menthol is dissolved in the essential oils as the oil phase; the water may be in range of 7±5% as aqueous phase; the long chain polymer surfactant includes the Tween 80 and the Tween 20 in volume/volume ratio of 90:20 to 20:90; the co-surfactant may be one or more of an alcohol including an extract which is medicated by one or more of *Vitex negundo, Boswellia serrata* fibromyalgia, sarcoidosis, gout, pseudogout, spondyloarthropathies, ankylosing spondylitis, reactive arthritis, psoriatic arthropathy, enteropathic spondylitis, reactive arthropathy, vasculitis, polyarteritis nodosa, Henoch-Schönlein purpura, serum sickness, Wegener's granulomatosis, giant cell arteriti, temporal arteritis, Takayasu's arteritis, Behçet's syndrome, Kawasaki's disease (mucocutaneous lymph node syndrome), Buerger's disease (thromboangiitis obliterans), Juvenile Idiopathic Arthritis (JIA) including a wide range joint disorders affecting Children, Rheumatic arthritis; Soft Tissue Rheumatism affecting the joints and structures around the joints including tendons, ligaments capsules, bursae, Stress Fractures, muscles, nerve entrapment, vascular lesions, ganglion, connective tissue abnormalities and localized soft tissues disorders, diseases affecting bones; Osteoporosis, osteomalasia, renal osteodystrophy, Fluorosis, Rickets, Congenital and familial Disorders affecting Joints; Hyperextensible joints; Ehlers-Danlos Syndrome, Achondroplasisa, Marfan's Syndrome, Osteomyelitis and Bone TB by steps including topically administering to all vertebrates including a human being, a therapeutically effective amount formulation.

In another embodiment of the invention, a process for preparing a formulation to treat rheumatic disorders and related infections is provided. The formulation is a microemulsion including one or more of an active ingredients; The active ingredient includes one or more of an of an essential The water in oil micro-emulsion may include winter green oil in an amount 20±3% as volume/volume, a camphor oil in an amount 5±3% as volume/volume, an *eucalyptus* oil in an amount 6±3% as volume/volume along with weight/volume range of the menthol in 5±3%. The menthol is dissolved in the essential oils as the oil phase; the water may be in range of 7±5% as aqueous phase; the long chain polymer surfactant includes the Tween 80 and the Tween 20 in volume/volume ratio of 90:20 to 20:90; the co-surfactant may be one or more of an alcohol including an extract which is medicated by one or more of *Vitex negundo, Boswellia serrata* oil mixed with an aqueous phase along with one or more of a surfactant and at one or more of a co-surfactant; and the co-surfactant is medicated by an extract of at one or more of a herbs. The process includes the steps of: mixing at one or more of the essential oil with 5 to 7 g w/v of menthol and 0.05±03% of *Capsicum Anuum* to obtain a mixture. The mixture is filtered with a 0.2 micron filter to obtain a filtrate; 30%±7% of the filtrate is mixed with 7%±5% of a water as the aqueous phase to obtain a mixture "A"; one or more of the surfactant are mixed in the weight ratios of 90:20 to 20:90 to obtain a mixture "B"; The "A" is emulsified with the 20%±10% of the mixture "B" to obtain an emulsified mixture; The emulsified mixture is stirred for 15 minutes under a inert atmospheric condition to obtain a Micro-emulsion; The micro-emulsion is mixed with 8%±5% of the surfactant to the obtained a transparent micro-emulsion "C"; 95%±5% of an alcohol is taken as the co-surfactant and is mixed with the extract of one or more of the herbs in equal proportions. The herbs are dissolved in 12 to 16, times volume of 95% of the alcohol to obtained a solution "D"; 35%±10% of the "D" is mixed into "C" to obtain a mixture "E"; a colloidal mill is used and the "E" is filtered to obtain a resultant micro-emulsion.

7%±5% of an alcohol may be added into "E" to saturate the co-surfactant.

The oil phase may include of one or more of the essential oil including a winter green oil, a camphor oil, an *eucalyptus* oil. The essential oil is mixed with the aqueous phase consisting of a water along with the surfactant tween 80, tween 20; and The co-surfactant is ethanolic and is medicated by an extract of *Vitex nigundo, Boswellia serrata* and *Apium graveolens*.

BRIEF DESCRIPTION OF DRAWINGS

The embodiments herein will be better understood from the following detailed description with reference to the figures and tables in which:

FIG. 2 illustrates table 2 showing a result of long term stability data of the formulation.

FIG. 6 illustrates table 4 showing efficacy of the formulation as compared to the other brand available in the market.

DETAILED DESCRIPTION OF THE PREFERRED EMBODIMENT

Figure 1:
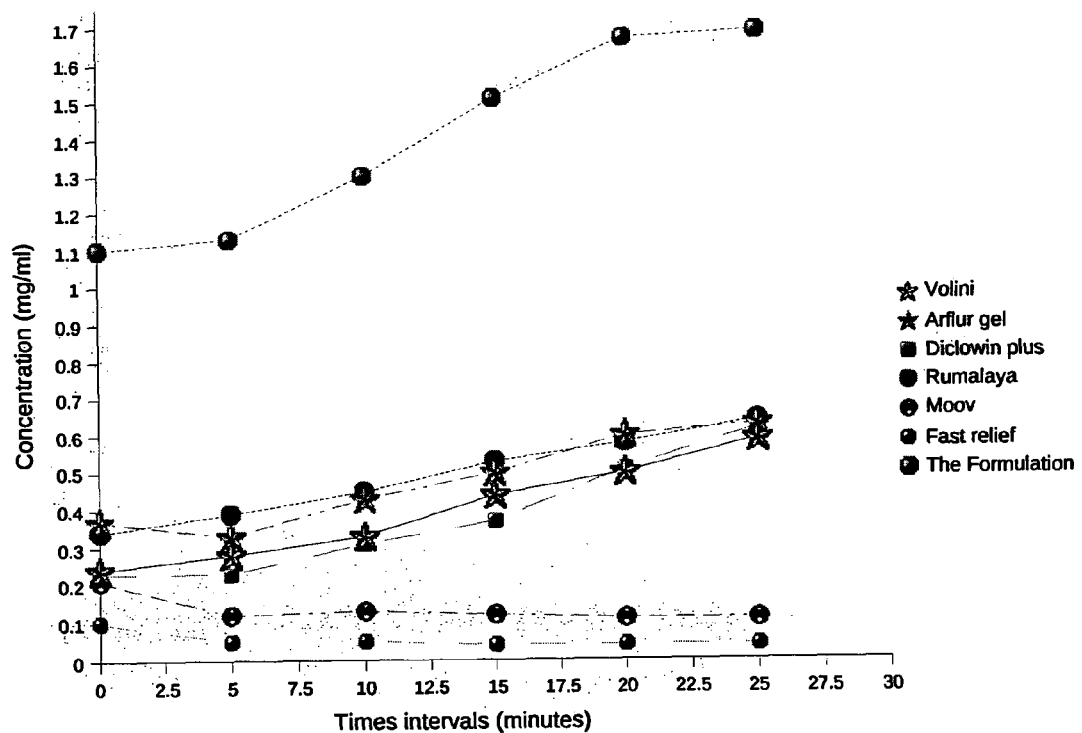
FIG. 1 illustrates table 1 showing a study result in vitro skin penetration of a formulation in the form of a micro-emulsion vis-a-vis six commercial brands taken from market.

The embodiments herein and the various features and advantageous details thereof are explained more fully with reference to the non-limiting embodiments that are illustrated in the accompanying figures & tables and detailed in the following description. Descriptions of well-known components and processing techniques are omitted so as to not unnecessarily obscure the embodiments herein. The examples used herein are intended merely to facilitate an understanding of ways in which the embodiments herein may be practiced and to further enable those of skill in the art to practice the embodiments herein. Accordingly, the examples should not be construed as limiting the scope of the embodiments herein.

As mentioned, there remains a need for a novel herbal formulations with novel delivery system for topical application, for the treatment and cure of all types of rheumatic disorders and related infections including arthritis, gout, fibromyalgia, ankylosing spondylitis, osteomyelitis, bone TB. Also an alternative solution for rheumatic disorders and related infections must be studied and developed in order to provide the best possible effect of natural substances on antibacterial, anti-inflammatory, analgesic, oxidative stress reducing action in these diseases using Novel drug delivery strategies (NDDS) have also been instrumental in optimizing efficacy of therapeutic agents by either modulating their biopharmaceutical properties and improving pharmacological effects or minimizing or eliminating the side effects associated with them, reducing treatment time thus offering better patient compliance.

The embodiments herein achieve this by providing a micro-emulsion based formulation comprising one or more essential oils in a particular weight ratio as oil phase and water as aqueous phase with at least one or more surfactants. The embodiments here stabilize therapeutically active agents by entrapping it in lipid phase consisting of one or more essential oils along with aqueous phase so as to make a stable, micro-emulsion with synergistic anti inflammatory, analgesic, bacteriostatic, anti oxidant, immuno modulatory action for topical application. Further, the herbal topical formulation is to have improved percutaneous penetration, excellent thermodynamic stability, low skin irritation, eliminates variability in absorption, provides protection from hydrolysis and oxidation as therapeutically active agents in oil phase in micro-emulsion are not exposed to attack by water and air ensuring long shelf life. The therapeutically active agents are lipophilic in nature According to one embodiment, a novel herbal formulations, their novel delivery mechanisms, compositions and process for the preparation of the same in pharmaceutical acceptable dosage forms is provided for its use for reducing/alleviating symptoms associated with rheumatic disorders and related infections. A non limiting examples of such disease include Rheumatoid arthritis, Lupus, Sjögren's syndrome, scleroderma (systemic sclerosis), dermatomyositis, polychondritis, polymyositis, polymyalgia rheumatica, osteoarthritis, septic arthritis, fibromyalgia, sarcoidosis, gout, pseudogout, spondyloarthropathies, ankylosing reactive arthritis, psoriatic arthropathy, enteropathic spondylitis, reactive anthropathy, vasculitis, polyarteritis nodosa, Henoch-Schönlein purpura, serum sickness, Wegener's granulomatosis, giant cell arteriti, temporal arteritis, Takayasu's arteritis, Behçet's syndrome, Kawasaki's disease (mucocutaneous lymph node syndrome), Buerger's disease (thromboangiitis obliterans), Juvenile Idiopathic Arthritis (JIA) including a wide range joint disorders, affecting Children, Rheumatic-arthritis; Soft Tissue-Rheumatism affecting the joints and structures around the joints including tendons, ligaments capsules, bursae, Stress Fractures, muscles, nerve entrapment, vascular lesions, ganglion, connective tissue abnormalities and localized soft tissues disorders, diseases affecting bones; Osteoporosis, osteomalasia, renal osteodystrophy, Fluorosis, Rickets, Congenital and familial Disorders affecting Joints; Hyperextensible joints; Ehlers-Danlos Syndrome, Achondroplasisa; Marfan's Syndrome, Osteomyelitis, Bone TB etc.

According to one embodiment, the formulation comprises one or more essential oils in a particular weight ratio as oil phase and water as aqueous phase with one or more non-ionic long chain polymer surfactants, and a co-surfactant. The co-surfactant is medicated and is an extract of one or more herbs in specific ratio and the herbs are active ingredients of the formulation.

The essential oils of the formulation includes a Wintergreen oil, an *Eucalyptus* oil, a Camphor oil, a *Cedrus* oil, a Sesame oil, a Terpentine oil, a Clove oil, a Garlic oil, a *Cyperus* oil, a Basil oil, a Lavender oil, a Rosemary oil, a *Gaultheria precumbens* oil, a *Cinnamomum camphora* oil, a Mint oil & a Geranium oil which are mixed with *capsicum annum* and/or menthol including, among other ingredients, one or more extracts of an herb of *Apium graveolens, Withania somnifera, Withania somnifera, Allium sativum, Myristica fragrans, Piper nigrum, Zingiber officinale, Piper longum, Cinnamomum zeylanicum, Cinnamomum tamala, Vitex negundo, Boswellia serrata, Cissus quadrangularis, Terminalia arjuna, Pluchea lanceolata, Commiphora mukul, Sida acuta, Cedrus deodara, Tinospora cordifolia, Cyperus rotundus, Trachyspermum ammi, Embelia ribes, Piper longum*. The given essential oils are systemically absorbed.

According to one embodiment, the formulation includes one or more therapeutically active ingredients. The therapeutically active ingredients are present in the formulation as one or more herbs which includes one or more herbal phytochemicals as one or more essential oil such as a methyl salicylate, an eucalyptol (1,8-cineole), a Camphor, a Safrole, a Camphene, an Eugenol, a limonene, a β-selinene, a Triacontane, a Formaldehyde, a Gaultheriline, an Eugenol, a Terpineol, a Menthenone, a Borneol, a Capsaicin, a Citronellol, a Carvacrol, a Fenchene, a Phellandrene, a Bisabolene, a Cadinene, a Caprylic acid, a Rosmarinic acid, a Terpinen-1-ol, an alpha-pinene, a p-cymene & an Aromadendrene and a Boswellic acids and a humulene, a Viridiflorol; a squalene; and as extracts such as a 5-hydroxy 3,6,7,3',4'-pentamethoxy flavone; a 5-hydroxy 3,7,3',4'-tetramethoxy flavone; a 5,3'-dihydroxy 7,8,4'-trimethoxy flavanone; a p-hydroxy benzoic acid; a 3,4-dihydroxy benzoic acid; a luteolin 7-glucoside; a isoorientin; an agnuside; and, 2'-p-hydroxy benzoyl mussaenosidic acidv gum, tannins, beta sitosterol, lignin and terpenoids according to one embodiment herein. In one embodiment, in addition to the phytochemicals, the herbs also have minerals, vitamins and micro nutrients as important constituents which provides synergy to the formulations by improving pharmacological efficacy. The formulation is indicated for prophylaxis and therapy of joint and connective tissue disorders in vertebrates.

The oxidation of phytochemicals which are therapeutically active is prevented from degradation due to oil phase of the micro-emulsion according to an embodiment herein. in one embodiment the ratio of oil:water is 4:1.

The non-ionic surfactant of the formulation is a long chain polymer surfactant component and co-surfactant is one or more of an alcohol, preferably an ethanol wherein the amount of non-ionic surfactant and co-surfactant selected in the ratio of 0.5:1 to 1:1.5 which is found to provide a stable micro-emulsion of the formulation according to one embodiment herein.

In one embodiment the non-ionic surfactants of the formulation are selected from a group comprising a Tween 80, a Tween 20, a Span 80, a Span 20, a Arkopal, a Cetomacrogol 1000, a Cetostearyl alcohol; a Cetyl alcohol, a Cocamide DEA, a Cocamide MEA, a Decyl glucoside, a Glyceryl laurate, a Lauryl glucoside, a NP-40, a Narrow range ethoxylate, a Nonoxynol-9, a Nonoxynols, an Octaethylene a glycol monododecyl ether, an Oleyl alcohol, a Pentaethylene glycol monododecyl ether, a Poloxamer, a Polyglycerol, a polyricinoleate, a Polyoxyethylene, a Sorbitan monostearate, a Sorbitan tristearate, a Stearyl alcohol & a Triton X-100 according to one embodiment herein. In one embodiment, the non-ionic surfactants include a Tween 80, a Tween 20 in the weight ratio of 90:20 to 20:90 along with the co-surfactant. The ratio of Tween 80 and Tween 20 could also be in the range of 50:50.

The co-surfactants of the formulation includes an alcohol, preferably an ethanol, a propanol and a IPA according to one embodiment herein. The co-surfactant additionally includes an extract of one or more of herbs such as *Vitex negundo, Boswellia serrata, Apium graveolens, Zingiber officinale, Piper longum, Cinnamomum zeylanicum, Cinnamomum tamala, Myristica fragrans, Allium sativum, Withania somnifera, Cissus quadrangularis, Embelia ribes, Trachyspermum ammi, Cyperus rotundus, Cedrus deodara, Sida acuta, Commiphora mukul, Pluchea lanceolata, Terminalia arjuna*. In one embodiment the co-surfactant is a ethanol with a medicated extract of *Vitex negundo, Boswellia serrata* and *Apium graveolens* in the ratio of 1:1:1.

According to one embodiment the formulation is provided as a water in oil type micro-emulsion which includes a fine particles of the essential oils. The fine particle of essential oil includes an effective amount of a Methyl salicylate, an Eucalyptol (1,8-cineole), a Camphor, a Safrole, a Camphene, a Menthenone which are derived from one or more of the Wintergreen oil, the *Eucalyptus* oil, the Camphor oil and the Manthol crystals, an aqueous medium and a physiologically acceptable emulsifier for dispersing the fine particles of the essential oils in the aqueous medium. The micro-emulsion additionally includes a medicated co-surfactant. The medicated co-surfactant includes a Boswellic acids, a gum, a tannins, a beta sitosterol, a lignin, a terpenoids, a Viridiflorol, a squalene, a beta-sitosterol, a 5-hydroxy 3,6,7,3',4'-pentamethoxy flavone, a 5-hydroxy 3,7,3',4'-tetramethoxy flavone, a 5,3'-dihydroxy 7,8,4'-trimethoxy flavanone, a p-hydroxy benzoic acid, a 3,4-dihydroxy benzoic acid, a luteolin 7-glucoside, a isoorientin, and a agnuside, and a 2'-p-hydroxy benzoyl mussaenosidic acid, a limonene, β-selinene, a humulene as alcoholic extract of one or more of herbs such as the *Boswellia serrata*, the *Apium graveolens*, the *Vitex negundo* etc. The formulation thus formed are applied topically and is indicated for the treatment of rheumatic disorders with symptoms of pain, inflammation, bacterial infections and related conditions including but not limited to rheumatoid arthritis, osteoarthritis, osteomyletis, bone TB, ankylosing spondylitis, septic arthritis, fibromyalgia and other related disorders for reducing the production of pro-inflammatory cytokines.

The formulation has a particle size in the range of 0.1 to 0.2 micron, a zeta potential≤−0.268 and a poly dispersity index (PDI)≤0.136. The negative Zeta potential and the PDI<1 indicates the thermodynamic stability of the micro-emulsion.

The formulation is found to be useful in inhibiting platelet or whole blood aggregation and blood inflammation-inducing enzymes (5-lipoxgenase, cylooxygenase-1 and cylooxygenase-2) and for scavenging toxic active oxygen species. An active oxygen free radical scavenging activity in the formulation is caused due to phytochemicals present *Cinnamomum camphora, Boswellia serrata, Vitex negundo, Eucalyptus globulus* according to an embodiment herein.

According to one embodiment, the formulation in the form of the micro-emulsion is found to be effective in treating a disease condition related to inflammation of joints in which the synovium is expanded by an infiltrate of cells—Lymphocytes, plasma cells and a variety of other cells, mostly mononuclear cells. The joint fluid is rich in polymorphonuclear leucocytes and the cartilage is destroyed by the advancing edge of synovial connective tissue called panus. Rheumatoid Arthritis and osteomyelitis are therefore a chronic multisystem disease of unknown etiology characterized chiefly by persistent inflammatory synovitis, usually involving peripheral joints in a symmetrical fashion, Cartilaginous destruction, Bony erosions and joint deformation and hallmarks of persistent synovial hyperboles and hyperthrophy, lymphocytic infiltration of synovial tissue, joint infiltration by neutrophils, protease release and chondrocyte activation occur. Free radical damage is also believed to be the important factor in the pathophysiology.

As mentioned earlier, in one embodiment, the formulation includes essential oils as detailed in examples below as a oil phase along with aqueous phase and the long chain polymers used as non-ionic surfactants and is stabilized using ethanol as co-surfactant. The co-surfactant of the formulation additionally includes a medicated extract of one or more herbs in predefined ratio as disclosed in examples below.

In one embodiment, the formulation is a water in oil micro-emulsion which is thermodynamically stable and ensures long shelf life to the formulations. The particle size of the micro-emulsion range between 0.005 to 0.5 microns with PDI index between 0.100 to 0.300 and Zeta potential between −0.100 to −0.500, more preferably particle size is ≤0.5 micron, PDI index is ≤0.150 and Zeta potential is ≤−0.300. The micro-emulsion formulations are energy efficient and are made as water in oil type micro-emulsion in range of 1:4 to 4:1 One having ordinary skill in the art will readily recognize that the above ratios, ranges and concentrations may be varied and the effect or results may be readily gaged without departing from the spirit and scope of the present invention.

In another embodiment, the formulation is a water in oil type micro-emulsion consist of volume/volume range of winter green oil in 20±3%, camphor oil in 5±3%, *eucalyptus* oil in 6±3% along with weight/volume range of menthol in 5±3% dissolved in above mentioned mixture of essential oils as oil phase; water in range of 7±5% as aqueous phase along with long chain polymer surfactants with volume/volume range of Tween 80:Tween 20 is 88:12 and ethanol as co surfactant which is medicated extract of *Vitex negundo, Boswellia serrata* and *Apium graveolens* in the ratio of 1:1:1. The formulation thus made has optical transparency with particle size in the range of ≤0.005 micron, zeta potential is ≤−0.268 and poly dispersity index is ≤0.136. The said formulation is easy to manufacture, reproducible and results in spontaneous micro emulsion if the ratios and proportions are maintained.

In an alternate embodiment, the formulation is a water in oil type micro-emulsion including volume/volume range of *Gaultheria precumbens* oil in 13±3%, *Cedrus deodara* oil in 1±3%, *Cyperus rotundus* oil in 1±3%, *Cinnamomum camphora* oil in 4±3%, *eucalyptus* oil in 7±3% along with weight/volume range of *Capsicum anuum* in 0.05±3% and menthol in 4±3% dissolved in above mentioned mixture of essential oils as oil phase and water in range of 7±5% aqueous phase along with long chain polymer surfactants with volume/volume range of Tween 80:Tween 20 is 50:50, and ethanol as co surfactant which is medicated having extract *Apium graveolens* where the ratio of surfactant to co surfactant is 0.56:1 with HLB value of 16.7. The formulation thus made has particle site in the range of ≤0.5 micron, zeta potential is ≤−0.350 and poly dispersity index is ≤0.150.

According to one embodiment, the formulation is also found to be effective in reducing oxidative stress and has active free radical scavenging activity, bacteriostatic action against a wide range of microorganisms, improves blood flow, causes improvement in rheumatic factor, erythrocyte sedimentation rate, inhibit platelet/whole blood aggregation and inflammation-inducing enzymes (5-lipoxgenase, cylooxygenase-1 and cylooxygenase-2), Pro-inflammatory cytokines (such as TNF-a, IL-1b, IL-6, IL-10), eliminates inflammation, pain, fever and related disease conditions.

The micro-emulsion form of the formulation is found to increase the rate of absorption, improves, percutaneous penetration, eliminates variability in absorption, helps solubilize lipophilic therapeutic agents such as the phytochemicals, increases bioavailability, helps in rapid and efficient penetration of the active moiety, provides protection from hydrolysis and oxidation as drug in oil phase because micro-emulsion is not exposed to attack by water and air, increases patient compliance and requires lesser amount of energy, thus making current invention technically advanced compared to other topical preparations detailed in prior art.

Some illustrative example of the formulations with their different composition could be the following:

Example 1

The illustrative composition (100 ml batch size) of the formulation includes *Gaultheria Precumbens* oil—40 ml v/v, *Cedrus Deodara* oil—10 ml v/v, *Cyperus Rotundus* oil—5 ml v/v, *Cinnamomum Camphora* oil—5 ml v/v, *Eucalyptus Globulus* oil—5 ml v/v, *Lavendula Officinalis* oil—5 ml v/v, *Syzygium Aromaticum* oil—5 ml v/v, *Ocimum Sanctum* oil—5 ml v/v, *Rosmarinus Officinalis* oil—5 ml v/v, *Pinus Roxbunghi* oil—5 ml v/v, Capsaicin—0.01%, Menthol (*Mentha arvensis* crystals)—10 g w/v.

Example 2

The illustrative composition (100 ml batch size) of the formulation includes as the oil phase of the micro-emulsion *Gaultheria Precumbens* oil—5 ml v/v, *Cedrus Deodara* oil—3 ml v/v, *Cyperus Rotundus* oil—3 ml v/v, *Cinnamomum Camphora* oil—3 ml v/v, *Eucalyptus Globulus* oil—3 ml v/v, *Lavendula Officinalis* oil—3 ml v/v, *Syzygium Aromaticum* oil—3 ml v/v, *Ocimum Sanctum* oil—3 ml v/v, *Rosmarinus Officinalis* oil—5 ml v/v, *Pinus Rxburghi* oil—5 ml v/v, Capsaicin—0.01% and the water (Double distilled) as aqueous phase—10 ml v/v wherein the ratio of the oil phase and the water phase is 2:1; Menthol (*Mentha Arvensis* crystals)—5 g w/v; Surfactant (50% Tween 20 or 50% Tween 80) where HLB=15.8005—30 ml v/v; Co-surfactant (IPA)—20 ml v/v.

Example 3

The illustrative composition (100 ml batch size) of the formulation includes as the oil phase of the micro-emulsion-*Gaultheria Precumbens* oil—10 ml v/v, *Cedrus Deodara* oil—3 ml v/v, *Cyperus Rotundus* oil—3 ml v/v, *Cinnamomum Camphora* oil—4 ml v/v, *Eucalyptus Globulus* oil—4 ml v/v, Capsaicin—0.01% and the water (Double distilled) as aqueous phase—12 ml v/v wherein the ratio of the oil phase and the water phase is 2:1; Menthol (*Mentha arvensis* crystals) 4 g w/v; Surfactant (50% Tween 20 or 50% Tween 80) HLB=15.85—30 ml v/v; Co-surfactant (IPA) extracts of *Apium Araveolens, Withania Somnifera, Myristica Fragrans, Piper Nigrum, Cinnamomum Zeylanicum, Vitex Negundo, Boswellia Serrata, Cissus Quadrangularis, Terminalia Arjuna, Pluchea Lanceolata, Trachyspermum Ammi, Syzygium Aromaticum* all in same ratio to form—30 ml v/v.

Example 4

The illustrative composition (100 ml batch size) of the formulation includes as the oil phase of the micro-emulsion-*Gaultheria Precumbens* oil—9 ml v/v, *Cedrus Deodara* oil—4 ml v/v, *Cyperus Rotundus* oil—3 ml v/v, *Cinnamomum camphora* oil,—4 ml v/v, *Eucalyptus Globulus* oil—4 ml v/v, Capsaicin—0.01% and the water (Double distilled) as aqueous phase—12 ml v/v wherein the ratio of the oil phase and the water phase is 2:1; Menthol (*Mentha arvensis* Crystals)—4 g w/v; Surfactant (50% Tween 20 or 50% Tween 80) HLB=15.85—30 ml v/v; Co-surfactant (IPA) extracts of *Apium Araveolens, Withania Somnifera, Myristica Fragrans, Piper Nigrum, Cinnamomum Zeylanicum, Vitex Negundo, Boswellia Serrata, Cissus Quadrangularis, Terminalia Arjuna, Pluchea Lanceolata, Trachyspermum Ammi, Syzygium Aromaticum* all in same ratio to form—30 ml v/v.

Example 5

The illustrative composition (100 ml batch size) of the formulation includes as the oil phase of the micro-emulsion—*Gaultheria Precumbens* oil—14.57 ml v/v, *Cedrus Depdara* oil—0.81 ml v/v, *Cyperus Rotundus* oil—0.81 ml v/v, *Cinnamomum Camphora* oil—2.43 ml v/v, *Eucalyptus Globulus* oil—2.43 ml v/v, Capsaicin—0.050 g w/v, Menthol (*Mentha Arvensis* crystals)—2.43 g w/v and the water (Double distilled) as aqueous phase—11.74 ml v/v wherein the ratio of the oil phase and the water phase is 2:1, Surfactant (50% Tween 20 or 50% Tween 80) HLB=15.85—32.38 ml v/v; Co-surfactant (95% Ethanol) extracts of *Apium Graveolens, Vitex Negundo, Boswellia Serrata, Pluchea Lanceolata & Trachyspermum Ammi* all in same ratio to form—32.38 ml v/v (q.s.).

Example 6

The illustrative composition (100 ml batch size) of the formulation includes as the oil phase of the micro-emulsion—*Gaultheria Precumbens* oil—13.5 ml v/v, *Cedrus Deodara* oil—0.75 ml v/v, *Cyperus Rotundus* oil—0.75 ml v/v, *Cinnamomum Camphora* oil—4.5 ml v/v, *Eucalyptus Globulus* oil—7 ml v/v, Capsaicin—0.090 g w/v, Menthol (*Mentha arvensis* crystals)—4.5 g w/v and the water (Double distilled) as aqueous phase of amount 7.27 ml v/v wherein the water is medicated with 10 g/70 ml of *Vitex Negundi* extract and wherein the oil phase and the water phase is 2:1; Surfactant (50% Tween 20/50% Tween 80) HLB=15.85-25.50 ml v/v; Co-surfactant (95% ethanol) medicated with 50 g/350 ml *Boswellia Berrata* extract—43 ml v/v (q.s.)+16.6 ml;

Example 7

The Preferred Composition of the Formulation

The illustrative composition (100 ml batch size) of the formulation includes as the oil phase of the micro-emulsion—*Gaultheria Precumbens* oil—17 to 19 ml v/v, *Cinnamomum Camphora* oil—5 to 7 ml v/v, *Eucalyptus Globulus* oil—6 to 8 ml v/v, Menthol (*Mentha Arvensis* crystals)—5 to 7 g w/v and the water (Double distilled) as aqueous phase—7.57 ml v/v wherein the ratio of the oil phase and the water phase is 4:1; Surfactant (90% Tween 20 or 20% Tween 80) HLB=16.7-22.71 ml v/v; Co-surfactant (95% ethanol)—26.49 ml+7.57 ml v/v (qs)=34 ml-15 g/240 ml (*Apium graveolens*+*Boswellia serrata*+*Vitex negundo:*:1:1:1). The percentage of active constituents in this formulation is about 69.72%.

Example 8

The illustrative composition (100 ml batch size) of the formulation includes as the oil phase of the micro-emulsion-*Cedrus Deodara* oil—0.75 ml v/v, *Cyperus Rotundus* oil—0.75 ml v/v, *Cinnamomum Camphora* oil—4.5 ml v/v, *Eucalyptus Globulus* oil—7 ml v/v, Capsaicin (*Capsicum Anuum*)—0.050 g w/v and the water (Double distilled) as aqueous phase—7.27 ml v/v wherein the water is medicated with 10 g/150 ml of *Vitex Negundi* extract and wherein the ratio of the oil phase and the water phase is 4:1; Surfactant (50% Tween 20 or 50% Tween 80) HLB-=16.7-25.50 ml v/v; Co-surfactant (95% ethanol) medicated with 20 g/250 ml of *Apium Graveolens*—43 ml v/v (q.s.).

Method of Preparation of the Formulation in the Form of the Micro-Emulsion

An illustrative method of preparation of the formulation as micro-emulsion is described below: In the first step all the oils (essential oils) as described in Example 7 are mixed along with 0.01±10% of menthol in an amount specified therein to obtain a mixture. *Capsicum Anuum* may also be added into the mixture in amounts 0.05±03% and then the resulting mixture is filtered with a 0.2 micron filter.

In the second step the filtrate obtained in the first is taken in an amount 30%±7% and is mixed with 7%±5% of water as aqueous phase. The mixture thus obtained is designated as "A".

In the third step one or more of surfactants as described in Example 7 are mixed in the weight ratios of 90:20 to 20:90. The mixture thus obtained is marked "B".

In the fourth step "A" is emulsified with the 20%±10% of surfactant mixture "B".

In the fifth step, the emulsified mixture obtained in step four is stirred for 15 minutes under a inert atmospheric condition to obtain a macro-emulsion.

In step six, remaining of surfactants in an amount 8%±5% is added to the micro-emulsion obtained in the last step to obtain almost transparent micro-emulsion. The transparent micro-emulsion thus obtained is designated as "C".

In step seven, separately 95%±5% of an alcohol, preferably ethanol is taken as co-surfactant and is mixed with extract of one or more of herbs such as *Apium graveoiens*, *Withania somnifera*, *Allium sativum*, *Myristica fragrans*, *Piper nigrum*, *Zingiber offcinale*, *Piper longum*, *Cinnamomum zeylanicum*, *Cinnamomum tamala*, *Vitex negundo*, *Boswellia serrata*, *Cissus quadrangularis*, *Terminalia arjuna*, *Pluchea lanceolata*, *Commiphora mukul*, *Sida acuta*, *Cedrus deodara*, *Tinospora cordifolia*, *Cyperus rotundus*, *Trachyspermum ammi*, *Embelia ribes*, *Piper longum* in equal proportions which are dissolved in 12 to 16 times volume of 95% ethanol, the solution thus obtained is designated as "D".

In the next step, 35%±10% of "D" is mixed into "C". The mixture thus obtained is designated as "E". 7%±5% more of ethanol may be added into "E" if needed to saturate the co-surfactant.

In the last step the a colloidal mill is used and the "E" is filtered. The resultant micro-emulsion is filled in suitable containers.

The micro-emulsion thus obtained is found to have the particle size of ≤0.05 micron. Steps involved in formulation include but are not limited to the disclosures made here in above.

FIG. 1 illustrates, table 1 showing a study result in-vitro skin penetration of a formulation in the form of a micro-emulsion vis-a-vis six commercial brands taken from market. The transdermal delivery of the formulation (example 7) as micro-emulsion when applied topically through the skin to the systemic circulation provides a convenient route of administration for a variety of clinical indications. For transdermal delivery of the formulation as micro-emulsion, stratum corneum (Indicated in FIG. 1) is the main barrier layer for permeation of drug. In order to circumvent the stratum corneum and to increase the flux through skin membrane, different approaches of penetration enhancement can be used. Drug-vehicle based enhancement methods such as drug selection, vesicles and particles, liposomes, prodrugs and ion-pairs, chemical potential of drug, eutectic systems, complexation are used in transdermal research as better alternative method to enhance permeation of drugs through skin. The objective of the study herein was to find out the in vitro skin penetration rate of the formulation as micro-emulsion and its comparison with various commercial brands taken from the market. This experiment was carried out in according Kumar et al., 2009. In this the penetration rate of the formulation as micro-emulsion (example 7) was found to have 5 times more higher than other brands available in the market. This is due to the fact that the formulation as micro-emulsion (example 7) is a micro-emulsion and it's particle size is very less as compared to others thus facilitating rapid skin penetration and better efficacy.

A clinical studies on inhibitory effect of the formulation (described later as example 7) on pain was conducted taking the formulation of example 7. The result obtained showed that the formulation as taken in the form of example 7, causes better reduction in uric acid and ESR levels when compared with a control untreated and another anti arthritis oil (Brand 1) along with reduction in treatment time due to improved penetration and better efficacy of the micro emulsion based current invention.

FIG. 2 Illustrates table 2 showing a result, of long term stability data of the formulation. The formulation was taken as 50 ml bottle for external application and was packaging was done by filling in 50 ml plastic off-white bottle and sealed with flip off aluminium seal. The test conditions was as: 30°

C.±2° C./65%±5% RH and storage conditions was maintained below 30° C. All procedure was carried out as per STP. The result obtained shows that the formulation was stable for a shelf life of 24 months.

Figures 3, 4:
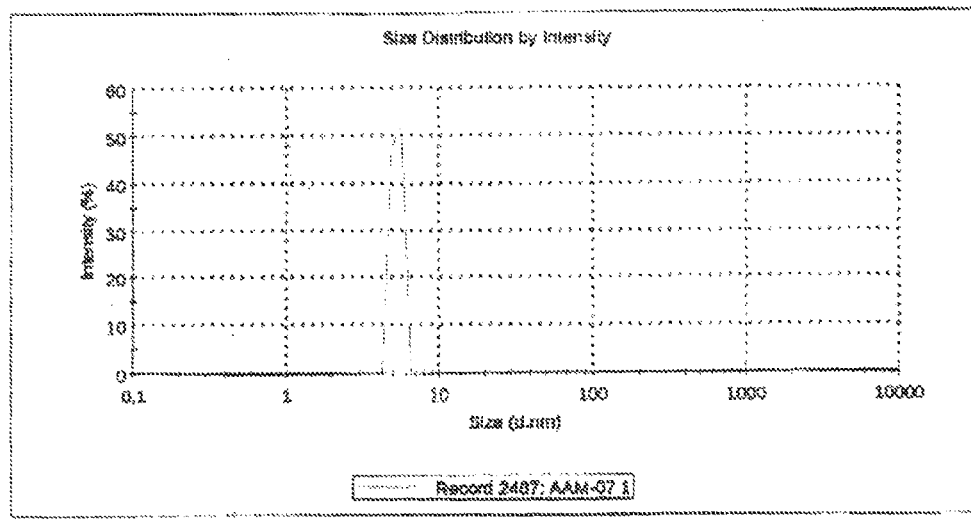
FIG. 3 illustrates table 3 showing a result of bactericidal activity of the Example 7 on *S. Aureus* and *E. coli* at a 3 different concentration by observing zone of growth inhibition in a antimicrobial susceptibility test.
FIG. 4 illustrates a graph showing a particle size distribution and a Poly Dispersity Index of a micro-emulsion form of the formulation.

FIG. 3 Illustrates table 3 showing a result of bactericidal activity of the Example 7 on *S. Aureus* and *E. coli* at a 3 different concentration by observing zone of growth inhibition in a antimicrobial susceptibility test.

FIG. 4 Illustrates a graph showing a particle size distribution and a Poly Dispersity Index of a micro-emulsion form of the formulation.

Figure 5:
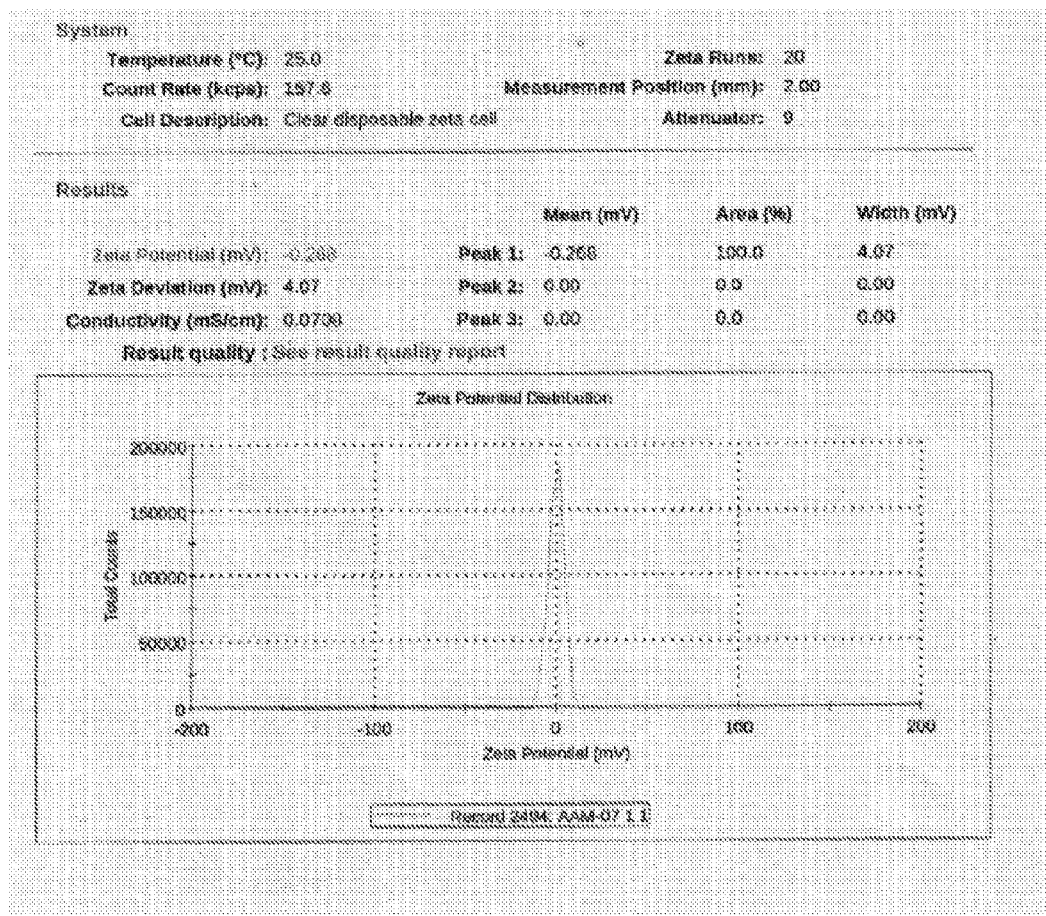
FIG. 5 illustrates a graph showing a Zeta potential of the micro-emulsion of the formulation.

FIG. 5 Illustrates a graph showing a Zeta potential of the micro-emulsion of the formulation.

In FIG. 6 Illustration of table 4 is given which shows efficacy of the formulation as compared to the other brands available in the market.

Above disclosure describe a manner and method of making using the invention and sets forth the not best mode contemplated by the inventor for carrying out his invention but is not to be construed as limiting. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications and equivalents of the described modes for carrying out the invention that are obvious to those skilled in formulation development or related fields are intended to be within the scope of the invention. The foregoing description of the specific embodiments will so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope of the appended claims.

What is claimed is:

1. A topical herbal formulation for treating rheumatic disorders, said formulation comprising:
    a micro-emulsion comprising at least one active ingredient;
    wherein said active ingredient comprises at least one essential oil mixed with an aqueous phase and a mixture of at least one surfactant and at least one co-surfactant;
    wherein said essential oil comprises *Gaultheria procumbens* oil which is present in an amount 20%±3% as volume/volume, camphor oil which is present in an amount 5%±3% as volume/volume, *eucalyptus* oil which is present in an amount of 6%±3% as volume/volume, and menthol which is present in an amount 5%±3% weight/volume;
    wherein said aqueous phase is present in the range of 7%±5%;
    wherein said co-surfactant comprises an extract of *Vitex negundo*, *Boswellia serrata* and *Apium graveolens*,
    wherein said *Vitex negundo*, *Boswellia serrata* and *Apium graveolens* are present in the proportion of 1:1:1 respectively; and
    wherein said formulation has a particle size of 0.005 micron to 0.5 micron; a zeta potential of −0.100 mV to −0.500 mV; and a poly dispersity index of 0.100 to 0.300.

2. The formulation of claim 1, wherein said oil phase and said aqueous phase are present in a ratio of 1:1 to 4:1.

3. The formulation of claim 1, wherein said surfactant and said co-surfactant are present in a ratio of 0.5:1 to 1:1.5.

4. The formulation of claim 1, wherein said aqueous phase consists essentially of water.

5. The formulation of claim 1, wherein said surfactant comprises at least one non-ionic long chain polymer selected from the group consisting of Tween 80, Tween 20, Span 80, Span 20, Arkopal, Cetomacrogol 1000, cetostearyl alcohol, cetyl alcohol, cocamide DEA, cocamide MEA, decyl glucoside, glyceryl laurate, lauryl glucoside, NP-40, an ethoxylate, nonoxynol-9, nonoxynols, octaethylene, glycol monododecyl ether, oleyl alcohol, pentaethylene glycol monododecyl ether, poloxamers, polyglycerol, polyricinoleate, polyoxyethylene, sorbitan monostearate, sorbitan tristearate, stearyl alcohol, and Triton X-100.

6. A topical herbal formulation for treating rheumatic disorders, said formulation comprising:
    a micro-emulsion comprising at least one active ingredient;
    wherein said active ingredient comprises at least one essential oil mixed with an aqueous phase and a mixture of at least one surfactant and at least one co-surfactant;
    wherein said essential oil is present as *Gaultheria precumbens* oil in an amount of 13%±3% as volume/volume, *Cedrus deodara* oil in an amount of 1%±3% volume/volume, *Cyperus rotundus* oil in an amount of 1%±3% volume/volume, *Cinnamomum camphora* oil in an amount of 4%±3% volume/volume, *eucalyptus* oil in an amount of 7%±3% volume/volume along with *Capsicum anuum* in an amount of 0.05%±3% weight/volume and menthol in an amount of 4%±3% dissolved in said essential oils as an oil phase;
    wherein said co-surfactant comprises an extract of *Apium graveolens*,
    wherein a ratio of said surfactant to said co-surfactant is 0.56:1 with an HLB value of 16.7; and
    wherein said formulation has a particle size in the range of 0.005 micron to 0.5 micron; a zeta potential of 0.100 mV to −0.500 mV; and a poly dispersity index of 0.100 to 0.300.

7. The formulation of claim 6, wherein said aqueous phase consists essentially of water.

8. The formulation of claim 7, wherein said surfactant comprises Tween 80 and Tween 20 in volume/volume ratio ranging from 90:20 to 50:50.

9. The formulation of claim 6, wherein said oil phase and said aqueous phase are present in a ratio of 1:1 to 4:1.

10. The formulation of claim 9, wherein said Tween 80 and Tween 20 are present in a volume/volume ratio from 90:20 to 50:50.

11. The formulation of claim 6, wherein said surfactant and said co-surfactant are present in a ratio of 0.5:1 to 1:1.5.

12. The formulation of claim 6, wherein said surfactant comprises at least one non-ionic long chain polymer selected from the group consisting of Tween 80, Tween 20, Span 80, Span 20, Arkopal, Cetomacrogol 1000, cetostearyl alcohol, cetyl alcohol, cocamide DEA, cocamide MEA, decyl glucoside, glyceryl laurate, lauryl glucoside, NP-40, an ethoxylate, nonoxynol-9, nonoxynols, octaethylene, glycol monododecyl ether, oleyl alcohol, pentaethylene glycol monododecyl ether, poloxamers, polyglycerol, polyricinoleate, polyoxyethylene, sorbitan monostearate, sorbitan tristearate, stearyl alcohol, and Triton X-100.

\* \* \* \* \*